US006919729B2

(12) United States Patent
Tiefnig

(10) Patent No.: US 6,919,729 B2
(45) Date of Patent: Jul. 19, 2005

(54) CORROSIVITY MEASURING DEVICE WITH TEMPERATURE COMPENSATION

(75) Inventor: Eugen Tiefnig, Berg/Drau (AT)

(73) Assignee: Rohrback Cosasco Systems, Inc., Santa Fe Spring, CA (US)

( * ) Notice: Subject to any disclaimer, the term of this patent is extended or adjusted under 35 U.S.C. 154(b) by 173 days.

(21) Appl. No.: 10/336,885

(22) Filed: Jan. 6, 2003

(65) Prior Publication Data

US 2004/0130340 A1 Jul. 8, 2004

(51) Int. Cl.⁷ .............................................. G01R 27/08
(52) U.S. Cl. ....................... 324/700; 324/71.1; 324/721
(58) Field of Search ............................... 324/71.1, 691, 324/700, 721

(56) References Cited

U.S. PATENT DOCUMENTS

| | | | |
|---|---|---|---|
| 3,821,642 A | * | 6/1974 | Seymour ..................... 324/700 |
| 4,587,479 A | * | 5/1986 | Rhoades et al. ............ 324/700 |
| 5,243,297 A | | 9/1993 | Perkins et al. |
| 5,627,749 A | | 5/1997 | Waterman et al. |
| 5,854,557 A | | 12/1998 | Tiefnig |

FOREIGN PATENT DOCUMENTS

EP          WO 00/54027          9/2000

* cited by examiner

Primary Examiner—Anjan Deb
Assistant Examiner—Timothy J. Dole
(74) Attorney, Agent, or Firm—John W. Renner; Renner, Otto, Boisselle & Sklar

(57) ABSTRACT

An improved corrosion measurement system for determining the rate of corrosion of a fluid medium. The system is comprised of a highly sensitive excitation and amplification electronic circuitry for registering and displaying the stable and accurate measurement results. A novel current feedback amplifier maintains a constant alternating current voltage across the reference element, by simultaneously controlling the current through the serially connected reference and corroding elements, thereby keeping the corrosivity measurement independent of the probe's ambient temperature. The unique unitized electrical resistance measurement probe is also temperature stabilized using thermally bridged and balanced metallic elements; the first reference element being coated with an impermeable insulating coating, the second, the sacrificial corroding element, being fully exposed to the corrosive fluid medium.

21 Claims, 11 Drawing Sheets

CORROSIVITY MEASURING DEVICE WITH TEMPERATURE COMPENSATION

FIELD OF THE INVENTION

The present invention relates primarily to an improved corrosion measurement system, and more particularly to a highly sensitive corrosion measurement system to determine the corrosivity and rate of corrosion in real-time without sacrificing accuracy and repeatability; the corrosion measurement system comprising a unique measuring and display unit and a novel unitized probe.

BACKGROUND OF THE INVENTION

Corrosion is a chemical reaction that involves the removal of metallic electrons from metals and formation of more stable compounds such as iron oxide (rust), in which the free electrons are usually less numerous. In nature, only rather chemically inactive metals such as gold and platinum are found in their pure or nearly pure form; most others are mined as ores that must be refined to obtain the metal. Corrosion is a process that simply reverses the refining process, returning the metal to its natural state. Corrosion compounds form on the surface of a solid material. If these compounds are hard and impenetrable, and if they adhere well to the parent material, the progress of corrosion is arrested. If these compounds are loose and porous, however, corrosion may proceed swiftly and continuously.

When two different metals are placed together in a solution (electrolyte), one metal will give up ions to the solution more readily than the other. This difference in behavior will bring about a difference in electrical voltage between the two metals. If the metals are in electrical contact with each other, electricity will flow between them and they will corrode—this is the principle of the galvanic cell or battery. Though useful in a battery, this reaction causes problems in a structure. For example, steel bolts in an aluminum framework may, in the presence of rain or fog, form multiple galvanic cells at the point of contact between the two metals, corroding the aluminum.

Corrosion testing is performed to ascertain the performance of metals and other materials in the presence of various electrolytes. Testing may involve total immersion, as would be encountered in seawater, or exposure to salt fog, as is encountered in chemical industry processing operations or near the oceans where seawater may occur in fogs. Materials are generally immersed in a 5 percent or 20 percent solution of sodium chloride or calcium chloride in water, or the solution may be sprayed into a chamber where the specimens are freely suspended. In suspension testing, care is taken to prevent condensate from dripping from one specimen onto another. The specimens are exposed to the hostile environment for some time, then removed and examined for visible evidence of corrosion. In many cases, mechanical tests after corrosion exposure are performed quantitatively to ascertain mechanical degradation of the material. In other tests, materials are stressed while in the corrosive environment. Still other test procedures have been developed to measure corrosion of metals.

Various testing methods have been utilized in the field of protection against corrosion.

A common method of corrosion measurement is by the method of measuring the loss in mass of the metallic specimen as it is immersed in the corrosive fluid medium. At precise periodic intervals, the test specimen is removed from the fluid medium and subsequently weighed to determine its instantaneous mass. It is then returned to the corrosive bath where the test is resumed. This method of determining the corrosion by a loss of mass is subject to errors in measurement if the temperature of the corrosive medium and the temperature of the specimen under test are not held constant, especially when the specimen is removed for the weight measurement. Fluid adhering to the specimen also contributes to the measurement errors.

Another common method of corrosion measurement is by electrical measurement, utilizing a direct current (DC current), where pieces of wire, tubes or disks are inserted into a corrosive medium and external electrical resistance measurements are taken. The reduction in size of the test object, increases the resistance of the specimen and therefore relates directly to the loss of metal by corrosion and/or erosion. One of the disadvantages of this test method is that the metals used for the specimen are quite temperature sensitive to the thermal gradients if the temperature of the corrosive fluid medium is not held constant. In many environments, such as in pipeline systems, the temperature variations are very extreme, which creates a large uncertainty and inaccuracy in measurement. Another disadvantage in this measurement technique derives from the fact that the specimen itself is subject to the galvanic action created between the specimen and the fluid medium; and, this galvanic voltage cannot be separated from the signal voltage.

Still another measurement method is by a change in inductance of the metallic specimen. To implement this procedure, a probe having a metallic core of steel or iron, encompassed by a coil of wire that conducts an alternating current (AC current), creates a magnetic field about the specimen. The measured impedance is subsequently separated into its quadrature components of inductive reactance and inductive resistance. The loss of metal then corresponds to the change in inductance. This method is advantageous in the reduction of errors due to galvanic action, but is disadvantageous because of the effects of temperature on the specimen and on the coil by the surrounding medium.

Examples of such prior art are shown in the examples that follow.

U.S. Pat. No. 5,854,557, granted Dec. 29, 1998, to E. Tiefnig, discloses an improved corrosion measurement system for determining the rate of corrosion of a metallic specimen immersed in a fluid medium. The system is comprised of a highly sensitive excitation and amplification electronic circuitry for registering and displaying the stable and accurate measurement results.

U.S. Pat. No. 5,583,426, granted Dec. 10, 1996, to E. Tiefnig, teaches of a method and apparatus for determining the corrosivity of fluids on a metallic material by means of passing an alternating current through a coil, having a predetermined frequency, amplitude and waveform, and a metallic specimen with identical composition to the metallic material exposed to the fluid. The specimen held within the magnetic field of the coil, sustains a loss of mass due to the exposure to the fluid media, which results in a change of inductance and inductive resistance.

U.S. Pat. No. 5,243,297, granted Sep. 7, 1994, to A. J. Perkins, et al., discloses an electrical resistance corrosion probe incorporating a temperature sensitive resistor that directly measures the temperature of the probe and of its environment as the corrosion measurements are being made. The temperature sensitive resistor has one end connected to the common junction between the test and reference elements of the corrosion probe and has its common line connected in the common line to several corrosion measuring circuits, including the test, reference and check circuits.

U.S. Pat. No. 4,426,618, granted Jan. 17, 1984, to C. Ronchetti, et al., discloses a probe for the continuous in-situ measurement of the rate of corrosion of pipes that are subjected to high temperatures or having high resistivity liquids flowing through.

U.S. Pat. No. 3,934,646, granted Jan. 27, 1976, to R. S. Robertson, et al., discloses a method and apparatus for determining the corrosion rate in the cold end of a boiler system, having a probe loop of an organic solvent circulating through the loop at a predetermined boiling temperature. A removable specimen is periodically tested for acid deposition or corrosion rate. Recirculating the organic solvent maintains the surface temperature of the specimen within close limits, approximating the maximum corrosion temperature.

The prior art recited above does not teach of the novel advantages that are found in the present invention.

It is therefore an object of the present invention to provide an improved corrosion measurement system that is comprised of a novel temperature compensated measurement circuit and a newly designed electrical resistance corrosion probe.

It is another object of the present invention to provide an improved corrosion measurement system that is comprised of a novel temperature compensated measurement circuit that utilizes the reference element within the corrosion probe as a temperature determining element.

It is still another object of the present invention to provide an improved corrosion measurement system that is comprised of a novel temperature compensated measurement circuit that utilizes the reference element within the corrosion probe as a temperature determining element of the surrounding fluid medium.

It is still yet another object of the present invention to provide an improved corrosion measurement system that is comprised of a novel temperature compensated measurement circuit that maintains the voltage across the reference element within the corrosion probe constant.

Yet still another object of the present invention is to provide an improved corrosion measurement system that is comprised of a novel temperature compensated measurement circuit that maintains the voltage across the reference element within the corrosion probe constant by utilizing current feedback to control the corrosion probe's excitation.

An additional object of the present invention to provide an improved corrosion measurement system that utilizes a unitized probe that houses physically matched elements by having the temperature gradient between the reference element and the corroding element, be near zero because of the thermal tracking due to the equality of the thermal inertia of the two masses.

It is a final object of the present invention to provide an improved corrosion measurement system that utilizes a unitized probe that incorporates physically matched elements that are thermally bridged to maintain a constant temperature gradient between the reference and the corroding elements.

These as well as other objects and advantages of the present invention will be better understood and appreciated upon reading the following detailed description of the preferred embodiment when taken in conjunction with the accompanying drawings.

SUMMARY OF THE INVENTION

The present invention relates primarily to an improved corrosion measurement system that is comprised of a newly designed measurement circuit and a novel measurement probe. This highly sensitive corrosion real-time measurement system determines the corrosivity and rate of corrosion simply, effectively and accurately with repeatable results.

The improved corrosivity measuring circuit is comprised of a feedback control loop whose input is derived from the corrosivity probe's reference element to maintain a constant voltage across the reference element. By maintaining a constant voltage across the reference element, the feedback regulator provides compensation for temperature variations in the measurement probe as well as providing compensation for temperature changes in the lines connecting the reference element.

In a second aspect of the present invention, self-calibration of the difference signal between the signal from the reference element and the signal from the sensor element is provided, both at zero and at full scale.

The measurement probe is comprised of two basic elements, a reference element and a corroding element. The reference element is conformably coated with a protective impermeable material to prevent the corrosive medium from etching or decomposing it, when the probe is immersed into the corrosive medium; whereas, the corrosion measurement element of the probe is not coated with the protective material and remains fully exposed to the corrosive medium. It is essential that the protective coating material has excellent thermal conduction transfer characteristics to obtain good thermal tracking readings between the reference element and the corroding element. Further, this coating must also have good electrical insulating properties.

Both electrodes, including the reference and the corroding elements, are made of the same metallic composition and of the same physical geometries, such as the mass, the diameter, the thickness, and the length. Because each electrode has near identical physical properties and are linked with a thermal bridge, the errors caused by thermal gradients are eliminated. The ratio of the voltages across each element is thermally compensating, thereby eliminating errors due to thermal tracking.

By utilizing the principles herein disclosed, a more rapid and stable measurement can be taken so that readout of the metal loss can be displayed accurately in real-time.

BRIEF DESCRIPTION OF THE DRAWINGS

The present invention is pictorially illustrated in the accompanying drawings that are attached herein.

DETAILED DESCRIPTION OF THE INVENTION

The present invention relates primarily to an improved corrosion measurement system. The system is comprised of a novel current feedback regulator and measurement circuit having a newly designed corrosivity probe. The current regulator is comprised of a feedback control loop whose input is derived from the corrosivity probe's reference element to maintain a constant voltage across the reference element. By maintaining a constant voltage across the reference element, the feedback regulator provides compensation for temperature variations in the measurement probe as well as providing compensation for temperature changes in the lines connecting the reference element. This highly sensitive corrosion measurement system determines the corrosivity and rate of corrosion simply, and presents the results in real-time to a digital display readout.

Figure 1:
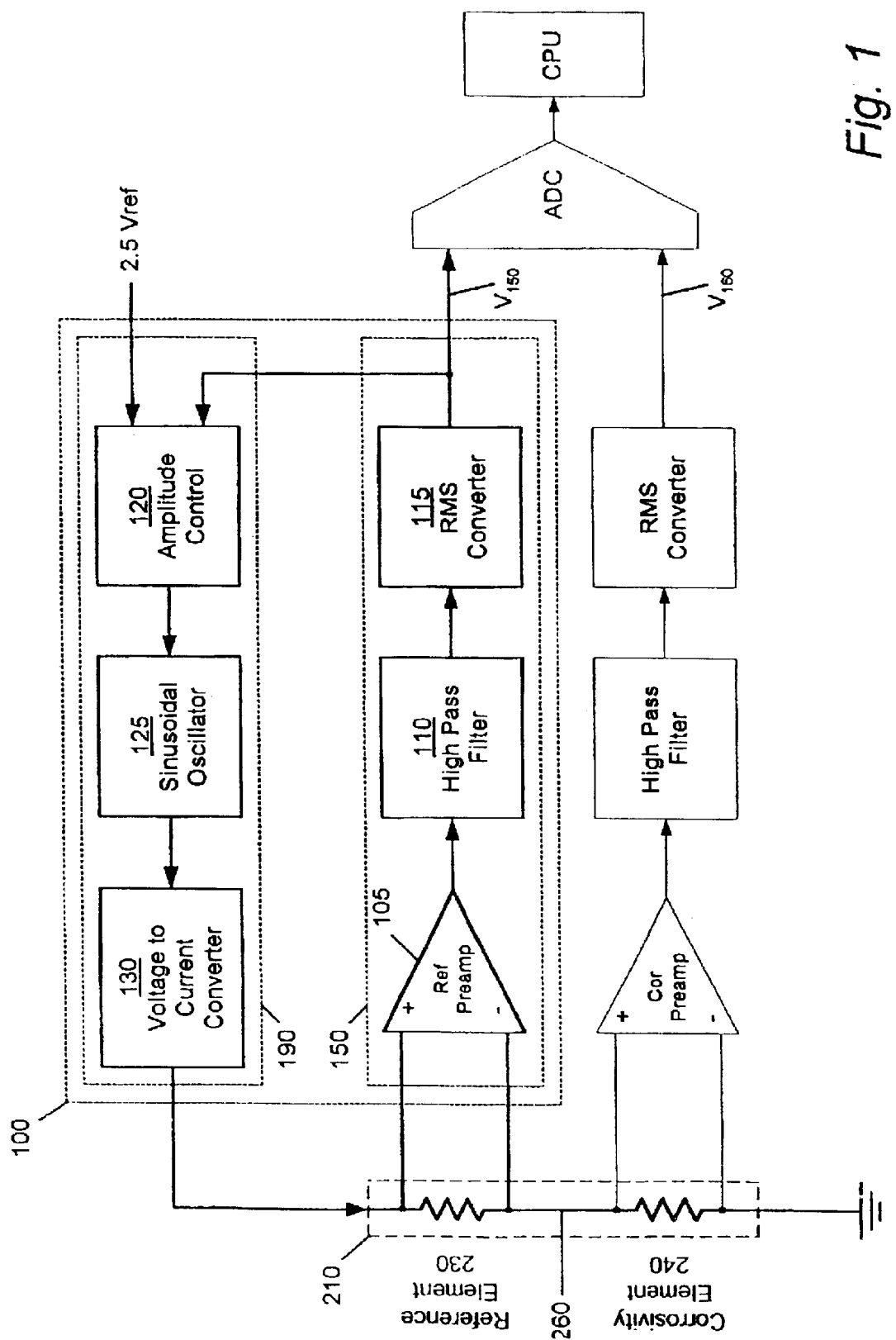
FIG. 1 is a functional block diagram of the present invention detailing the feedback control loop that maintains a constant voltage across the reference element.

As shown in FIG. 1, the reference element 230 is serially connected to the corroding element 240 via the thermal bridge 260. The sinusoidal voltage that appears across the reference element 230 is fed to the differential input of the feedback control circuit 100, where it is subsequently signal conditioned.

The current regulator feedback circuit 100 is comprised of the forward path channel 150 and the feedback channel 190.

The current regulator forward path channel 150 is comprised of differential reference amplifier 105, high pass filter 110, and RMS converter 115; The feedback path channel 190 comprises the amplitude control 120, sinusoidal oscillator 125 and voltage to current converter 130.

The input to the novel feedback control circuit 100 connects via the true differential input reference amplifier 105. The true differential reference amplifier 105 has an high input impedance to reduce the loading of reference element 230 to a minimum to maintain the reading accuracy. The common mode rejection of amplifier 105 is in excess of 90 db to reduce introducing a common mode error.

The high pass filter 110 connects to the output of differential amplifier 105. The pass band of the high pass filter is preferably 100 Hz., where it rejects all frequencies below its corner frequency. The purpose of the filter 110 is to reject all DC components, whether they are amplifier DC offsets, thermocouple voltages generated by the joining of two dissimilar metals or by galvanic action where two metals generate an EMF in the presence of an electrolyte.

The output of the high pass filter 110 connects to the RMS-to-DC converter 115, which extracts the root-mean-square voltage, which when filtered by using a low pass filter (not shown), converts the sinusoidal input to a DC voltage ($V_{150}$).

This DC voltage then connects to the feedback path channel 150, whose input is the amplitude control 120. The input to the amplitude control 120 is subsequently compared to an internal 2.5 volt DC reference voltage that is contained in the ADC converter 155. The difference between the two voltages, more commonly referred to as the error signal, then controls the amplitude of oscillation in the sinusoidal oscillator 125. The sinusoidal oscillator has a frequency range that ties preferably between 10 and 50000 Hz.

The voltage-to-current converter 130 converts the high impedance sinusoidal voltage from the output of sinusoidal oscillator 125, to a low impedance sinusoidal current, which subsequently connects to the serially connected resistive elements 230 and 240 that are contained within probe 210.

By maintaining a constant voltage drop across the reference element 230, the feedback regulator 100 compensates for temperature variations in the measurement probe 210, as well as compensating for temperature changes in the wires connecting the reference element.

Figure 2:
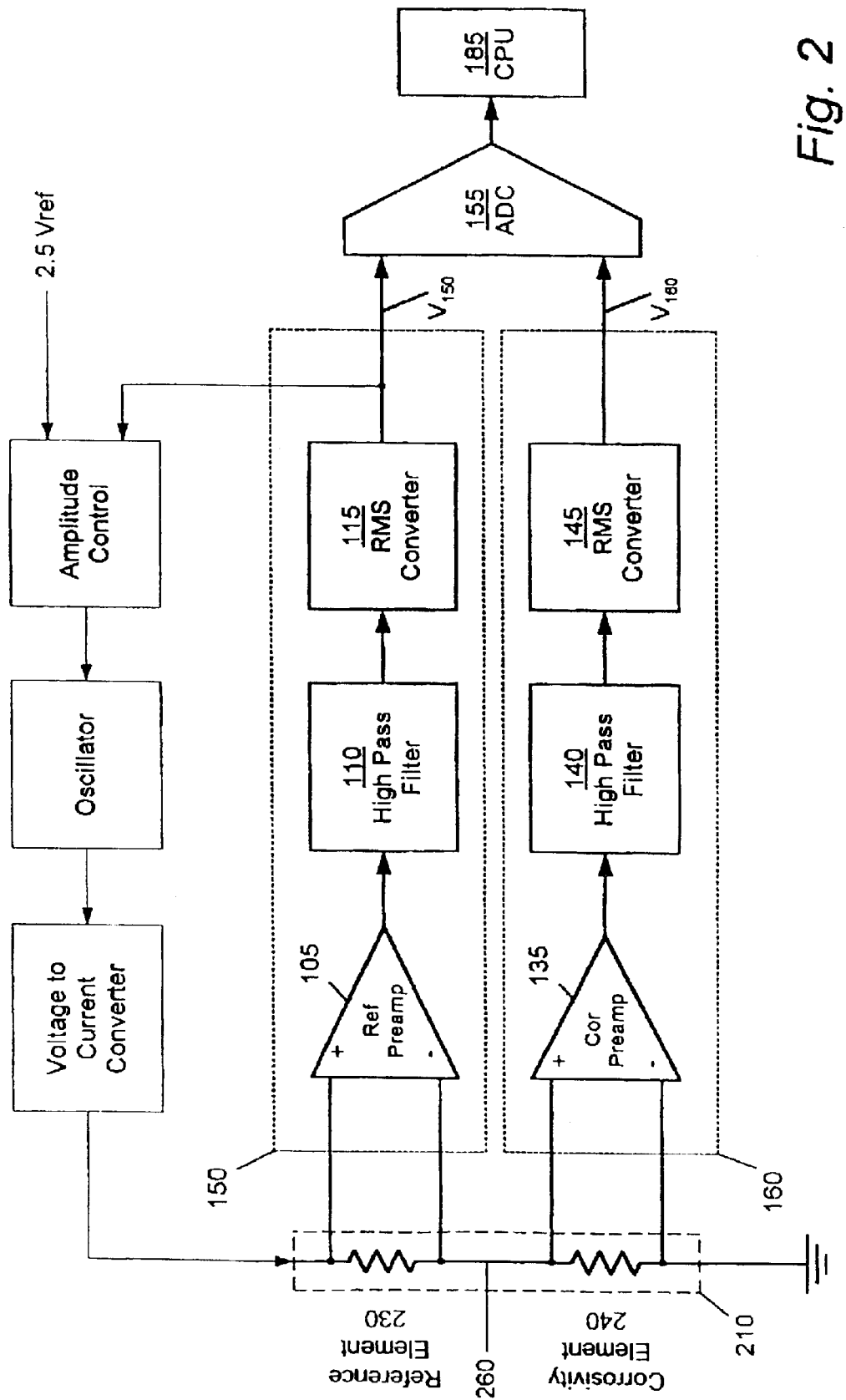
FIG. 2 is a functional block diagram of the present invention detailing the primary reference element signal conditioning and the corrosivity element measuring circuit signal conditioning.

Turning now to FIG. 2, there is shown the forward path reference measurement channel 150 and the forward path corrosion measurement channel 160. The forward path reference measurement channel 150 is comprised of differential reference amplifier 105, high pass filter 110, and RMS-to-DC converter 115. The forward path corrosivity measurement channel 160 is comprised of differential reference amplifier 135, high pass filter 140, and RMS-to-DC converter 145.

For the forward path reference measurement channel 150, the voltage across the reference element 230 connects to the input of the differential amplifier 105, where it then passes through the high pass filter 110 to remove all DC voltage components. Upon exiting the high pass filter the signal is converted to a DC voltage in RMS-to-DC converter 115, having a low pass filter connected to its output, where the low pass filter capacitor is not shown.

In the forward path corrosion measurement channel 160, the voltage across the corroding element 240 connects to the input of the differential amplifier 135, where it then passes through the high pass filter 140 to remove all DC voltage components. Upon exiting the high pass filter the signal is converted to a DC voltage in the RMS-to-DC converter 145, having a low pass filter connected to its output, where the low pass filter capacitor is not shown.

To maintain a high degree of thermal stability that is free from undesirable temperature excursions, the corrosion measurement channel 160 uses identical and matched components, that are the same as used in the reference measuring channel 150.

The outputs from each channel then connect to the analog-to-digital converter (ADC) 155, which is subsequently processed as a difference in the microprocessor 185 that follows.

Because it is necessary to accurately measure the temperature of the electrolyte in which the probe is immersed, a cold junction temperature reference channel 150 measures and stores the resultant measured value in the computer memory, where the measured value is kept for later retrieval.

The reference element 230 located with the sensor body is used as a temperature sensor, having a temperature coefficient of 3000 ppm./deg. C. The corrosion element 240, being closely matched to the reference element 230, also has a temperature coefficient of 3000 ppm./deg. C.

Figure 3:
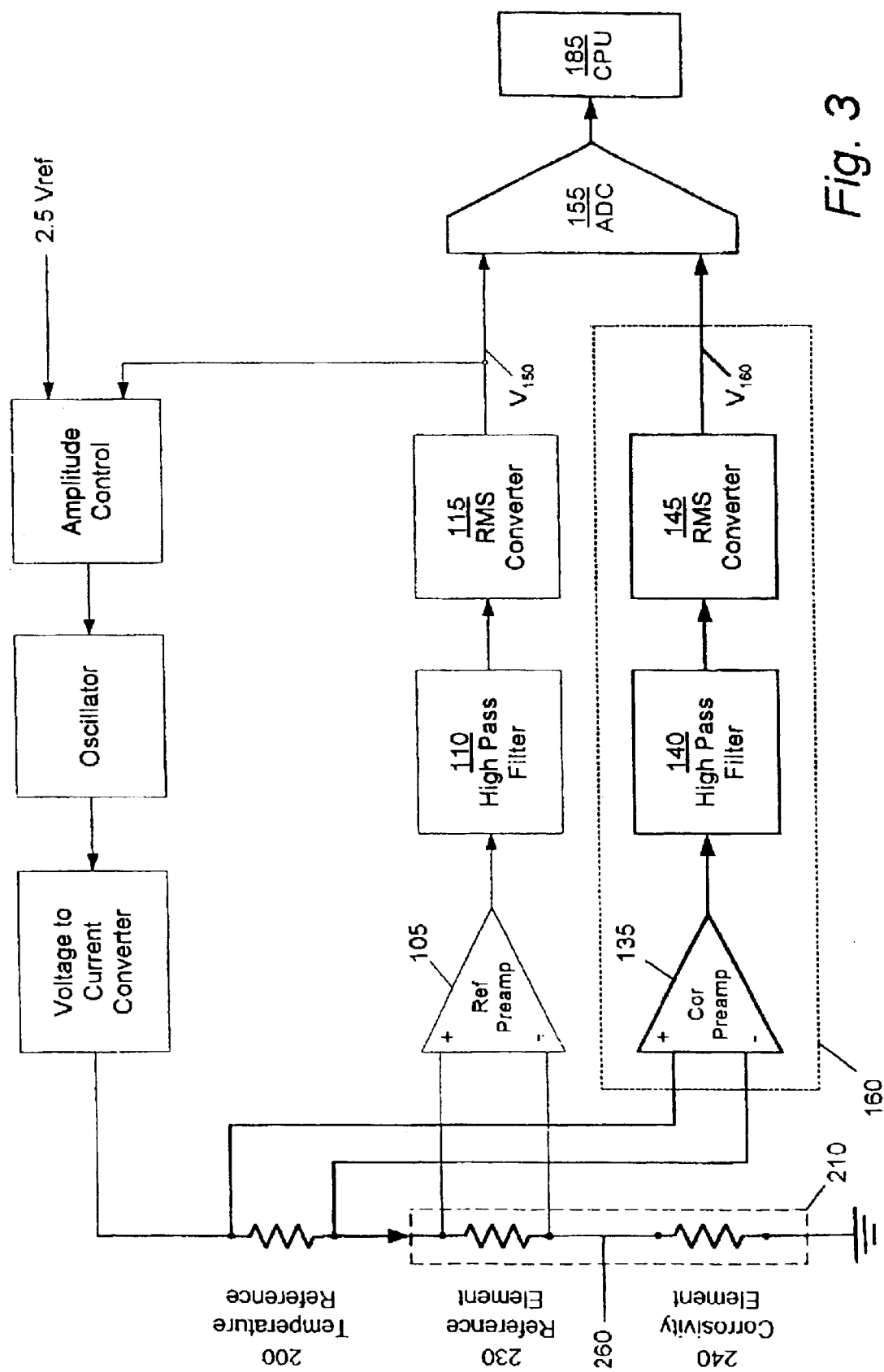
FIG. 3 is a functional block diagram of the present invention detailing the temperature reference measurement channel.

As shown in FIG. 3, the temperature reference element 200 is connected in series with the reference element 230 and the corroding element 240. All elements are driven from the same current source. The voltage across the temperature reference element 200 connects to the input of the differential amplifier 135, where it then passes through the high pass filter 140 to remove all DC voltage components. Upon exiting the high pass filter the signal is converted to a DC voltage in RMS-to-DC converter 145, having a low pass filter connected to its output, where the low pass filter capacitor is not shown. The output of channel 160 connects to the (−) input of the analog-to-digital converter 155.

The cold-junction temperature reference element 200, being located physically on the printed circuit board that contains all of the measurement circuitry, has a very stable temperature coefficient of 2 ppm./deg. C.

Figure 4:
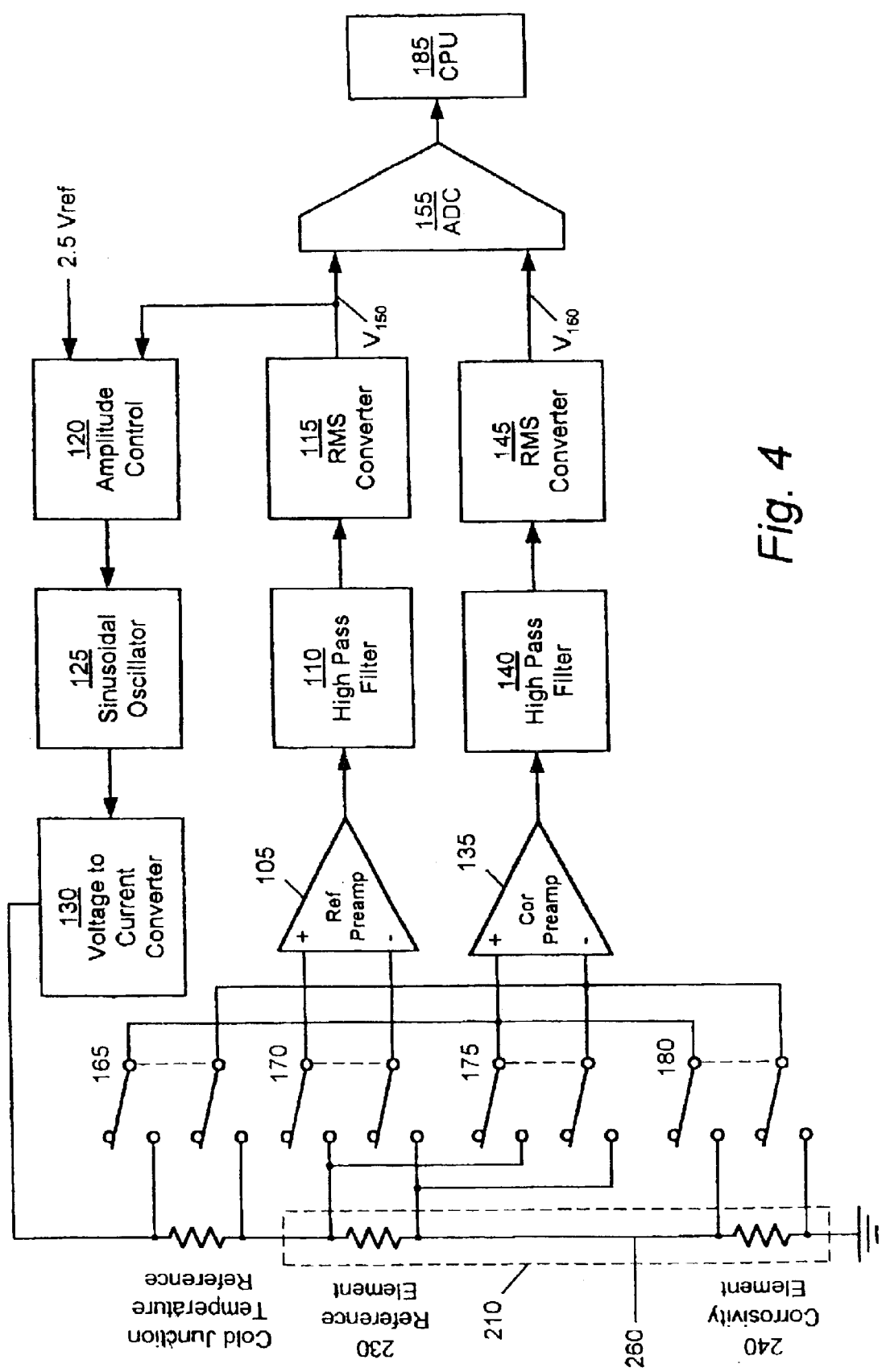
FIG. 4 is a composite functional block diagram that shows the detailed implementation of the feedback control loop, the forward path signal conditioning for the reference and the corrosivity channels and the reference temperature measurement channel.

FIG. 4 is a composite functional block diagram that integrates the functions that were previously described in FIGS. 1, 2 and 3. The relay contacts that arrange the computer controlled sequences are added to best illustrate and detail the switching arrangement relays.

In the preferred embodiment the relays depicted are monolithic CMOS devices, preferably, an Analog Devices, Inc. ADG412, which contains four independent SPST switches. This device provides for low power dissipation yet gives a high switching speed and a low ON resistance. The ON resistance profile is very flat over the full analog input range ensuring excellent linearity and low distortion when switching signals within the range of interest. Each switch conducts equally well in both directions when ON and each has an input signal range that extends to the supplies. In the OFF condition, signal levels up to the supplies are blocked. All switches exhibit a break-before-make switching action for use in this multiplexed switching application.

Relay contacts 170 serve to connect the signal derived across the reference element 230 to the input of the forward path reference signal conditioning channel 150. The forward path reference measurement channel 150 is comprised of a differential amplifier 105, a high pass filter 110, and a RMS-to-DC converter 115. The RMS-to-DC converter 115 is preferably an Analog Devices, model AD637 that is a complete high accuracy monolithic RMS-to-DC converter that computes the true RMS value of any complex waveform. The output from the forward path channel 150, $V_{150}$, connects to the positive input of the analog-to-digital converter 155 and to the input to the feedback path channel 190, (shown in FIG. 1).

The feedback path channel 190 is comprised of the amplitude control 120, a sinusoidal oscillator 125 and a voltage-to-current converter 130.

The DC signal voltage applied to the input of the amplitude control 120 is compared to an internal 2.5 volt DC reference voltage. The difference between the two voltages then controls the amplitude of oscillation in the sinusoidal oscillator 125 by controlling a FET amplifier that serves as an AGC device.

The sinusoidal oscillator 125 is preferably a Wien Bridge sinusoidal oscillator having a frequency range that lies preferably between 10 and 50000 Hz.

The voltage-to-current converter 130 converts the high impedance sinusoidal voltage from the output of sinusoidal oscillator 125, to a low impedance sinusoidal current, which subsequently connects to the serially connected resistive elements 230 and 240 that are contained within probe 210.

The current regulator 100 thereby maintains a constant voltage across the reference element 230 by controlling the current flowing through the reference element 230. By maintaining a constant voltage across the reference element 230, the feedback regulator 100 provides compensation for temperature variations in the measurement probe 210, as well as providing compensation for temperature changes in the lines connecting the reference element.

Because the reference element 230, the corroding element 240 and the cold-junction temperature reference 200 are all serially connected, each has the identical current passing through them.

The signal derived across the corroding element 240 connects to the input of the forward path reference signal conditioning channel 160 via relay contacts 175. The forward path corrosivity measurement channel 160 is comprised of differential reference amplifier 135, high pass filter 140, and RMS-to-DC converter 145.

The analog-to-digital converter 155 is an Analog Devices model ADC7712 Analog-to-Digital Converter, which has two analog input channels that will accept low level signals directly, and output a serial digital word to the microprocessor (CPU) 185, where the data is processed.

Figure 5:
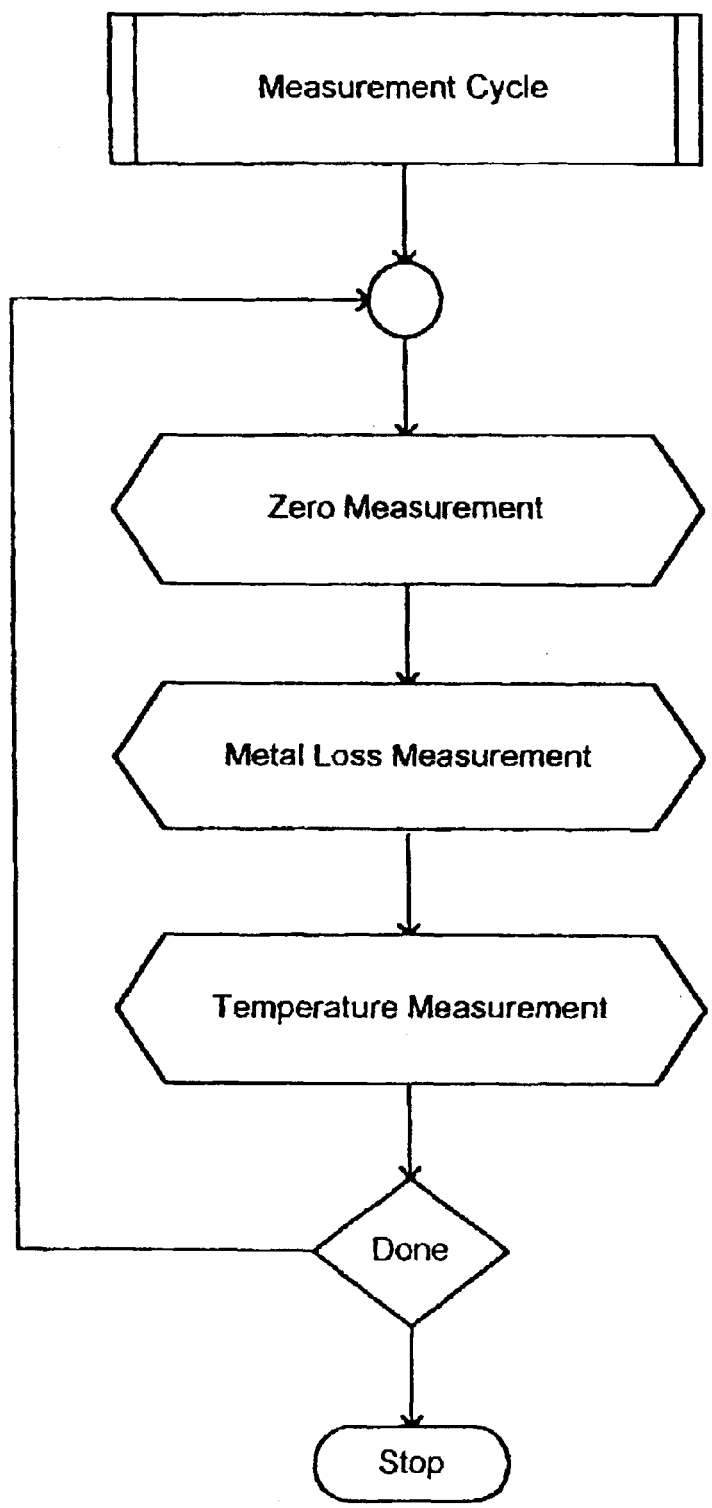
FIG. 5 is a signal flow diagram illustrating the measurement control cycle.

FIG. 5 is a signal flowchart that illustrates the measurement control cycle. The control loop performs the following sequences repetitively: (1) measures the zero offset in the reference and corrosivity forward path signal conditioners, 150 and 160 respectively, (2) measures and calculates the metal loss in the corrosion element 240 and (3) measures and calculates the temperature as measured at the probe 210.

Figure 6:
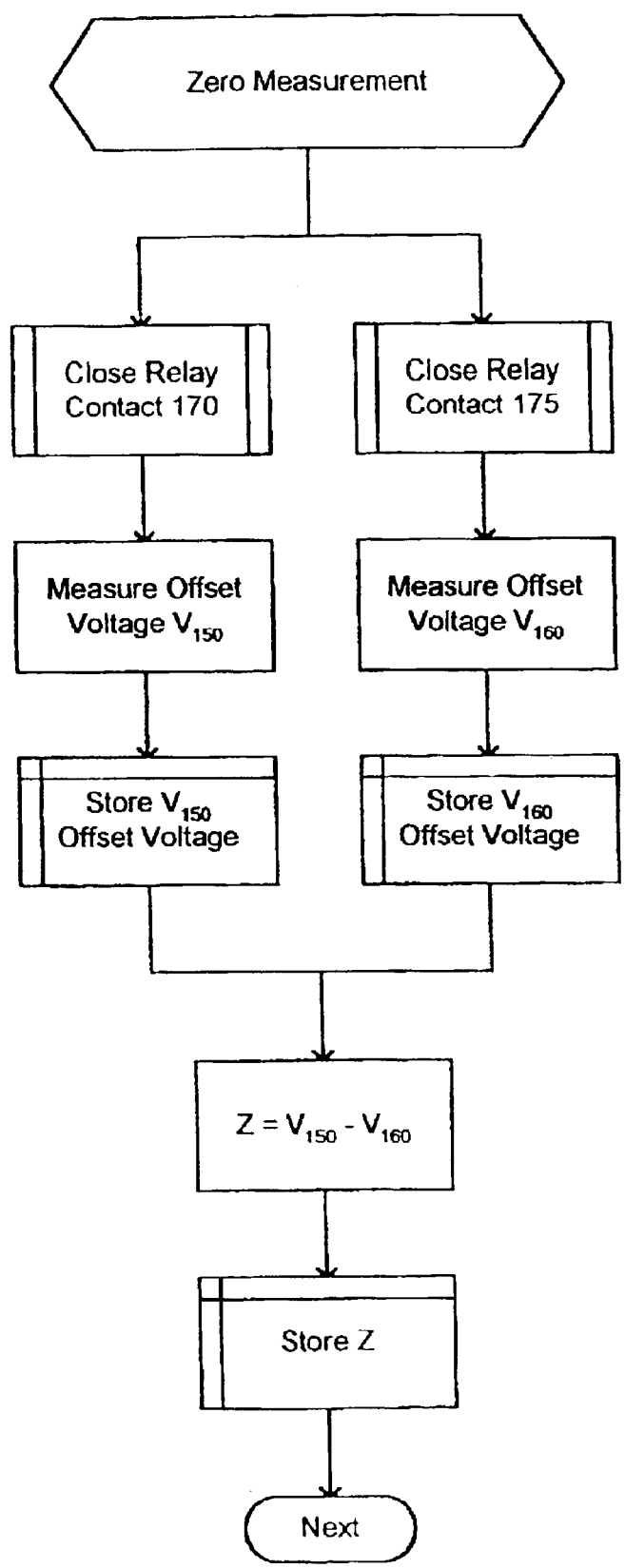
FIG. 6 is a signal flow chart illustrating the zero measurement cycle.

FIG. 6 is a signal flowchart that illustrates the measurement control cycle, where the zero offset in the reference and corrosivity forward path signal channels, 150 and 160 respectively, is measured and subsequently stored in memory.

The zero offset is determined by connecting the inputs to the reference channel 150 and the inputs to the corrosion channel 160 across the reference element 230. The zero offset is then obtained by subtracting the voltage $V_{160}$ from the voltage $V_{150}$.

Figure 7:
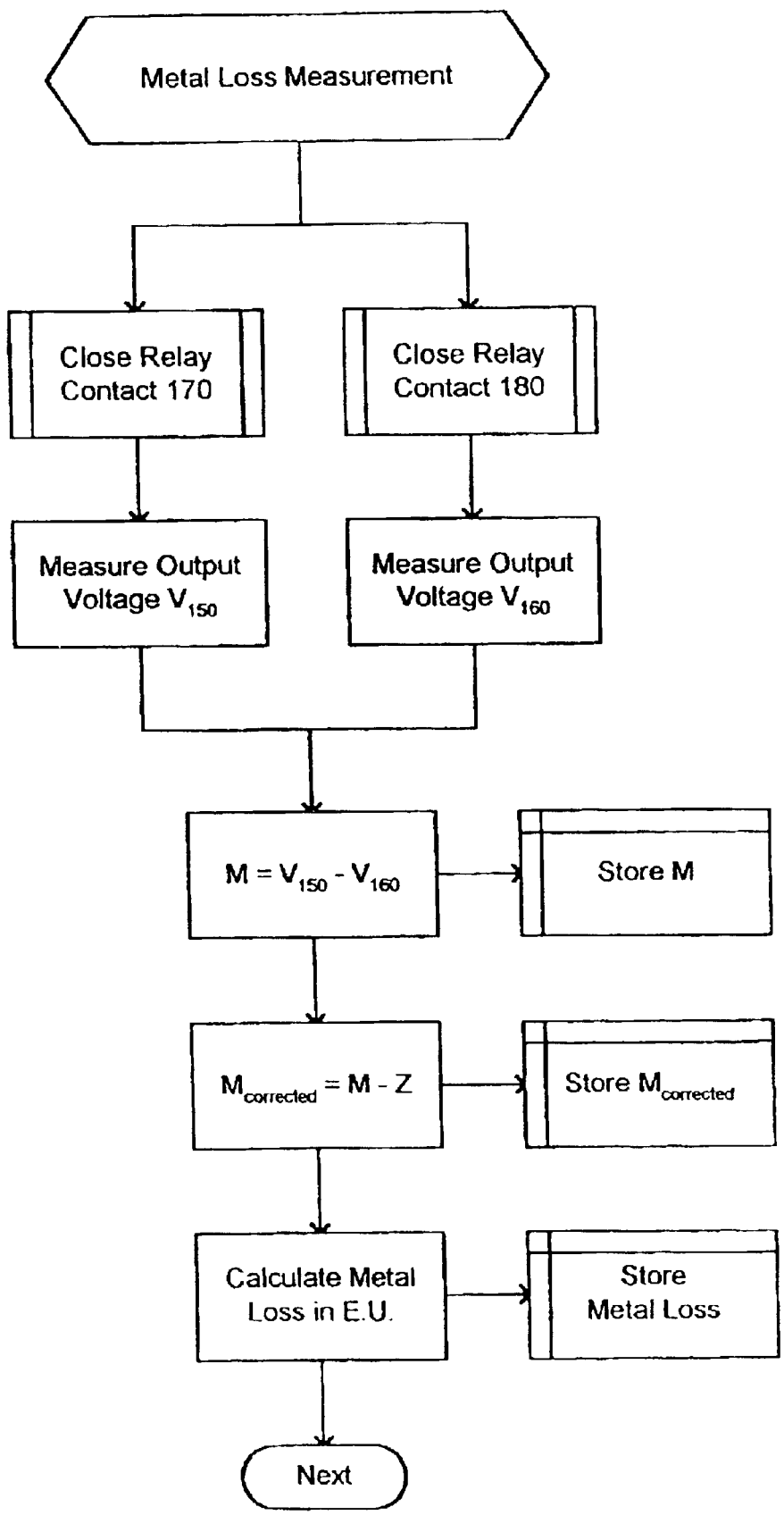
FIG. 7 is a signal flow chart illustrating the metal loss measurement cycle.

FIG. 7 is a signal flowchart that illustrates the measurement control cycle, where the metal loss in the corrosion element 240 is measured and the calculated result in engineering units is stored in memory.

For the metal loss measurement cycle, the loss of metal of the probe is obtained by subtracting the voltage $V_{160}$, as measured by determining the voltage across the corroding element 240 from the voltage $V_{150}$, as measured by determining the voltage across the reference element 230.

Figure 8:
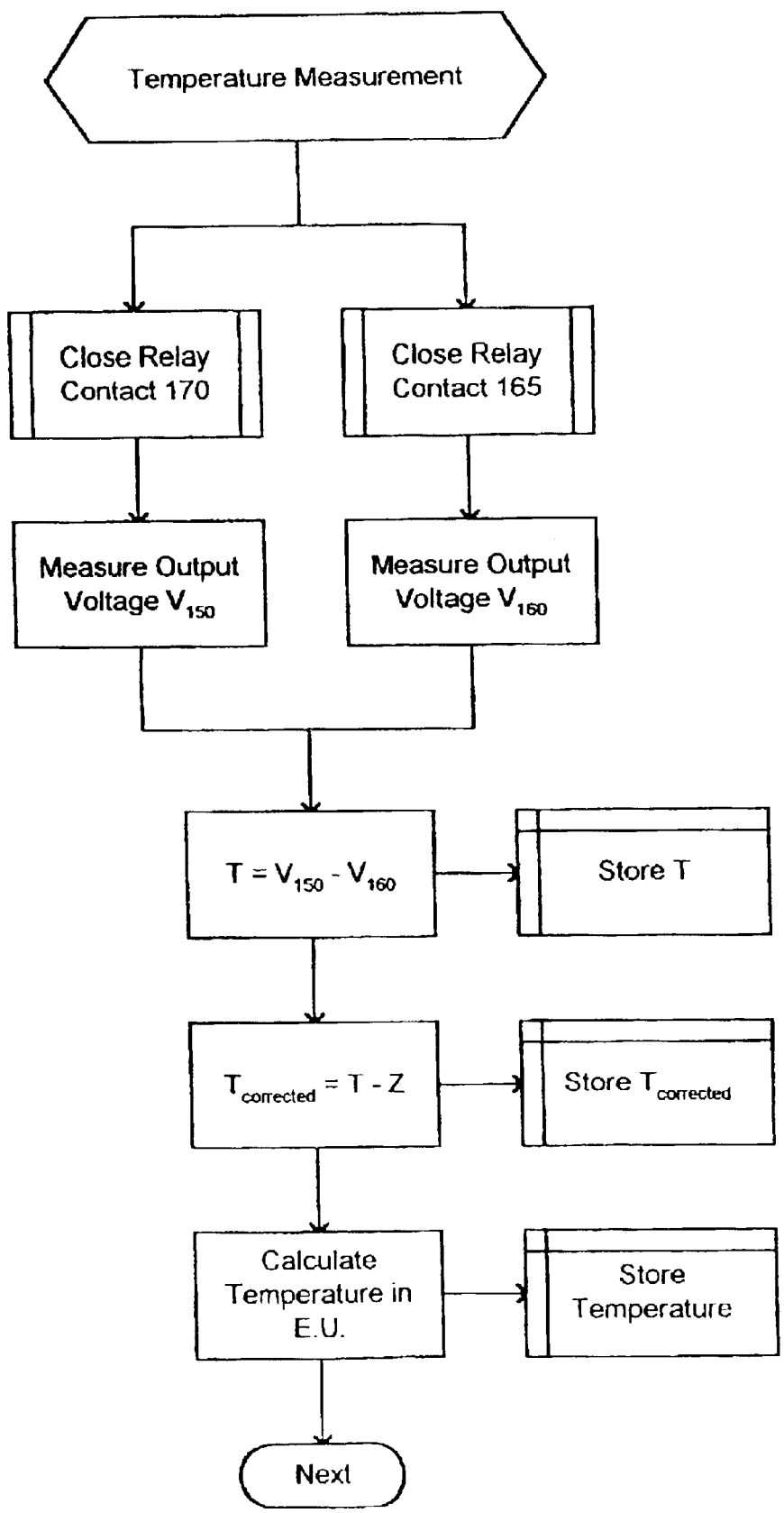
FIG. 8 is a signal flow chart illustrating the corrosivity probe temperature measurement cycle.

FIG. 8 is a signal flowchart that illustrates the measurement control cycle, where the temperature within the corrosivity probe is measured, converted to engineering units and the result stored in memory.

For the temperature measurement cycle, the temperature of the probe is obtained by subtracting the voltage $V_{160}$, as measured by determining the voltage across the cold-junction temperature reference element 200 from the voltage $V_{150}$, as measured by determining the voltage across the reference element 230.

Figure 9:
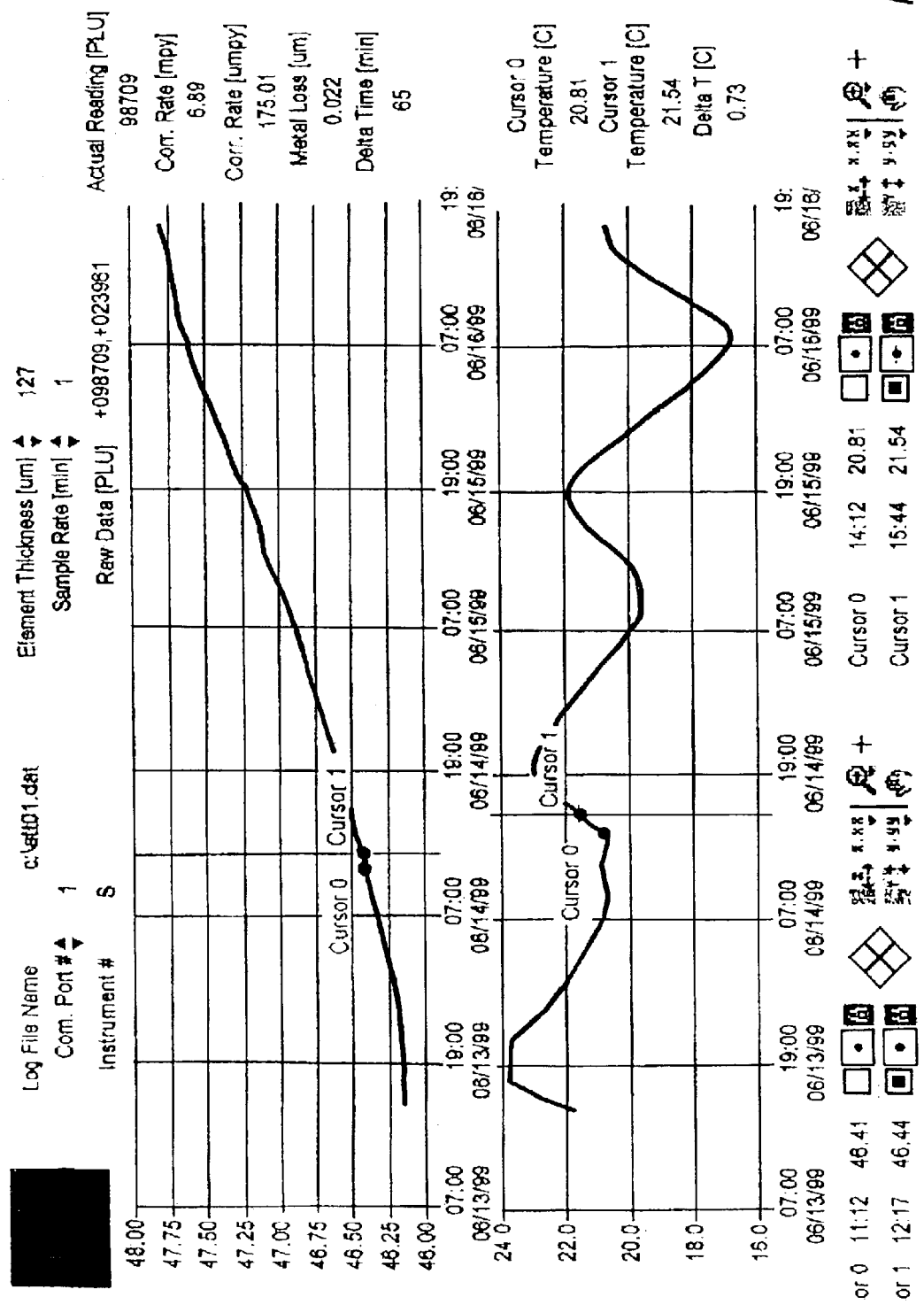
FIG. 9 is a performance graph that best shows the typical results that were obtained of thee metal loss and temperature as a function of time.

The sensitivity and repeatability of measurement are clearly shown in the accompanying graphical results shown in FIG. 9.

Figure 10:
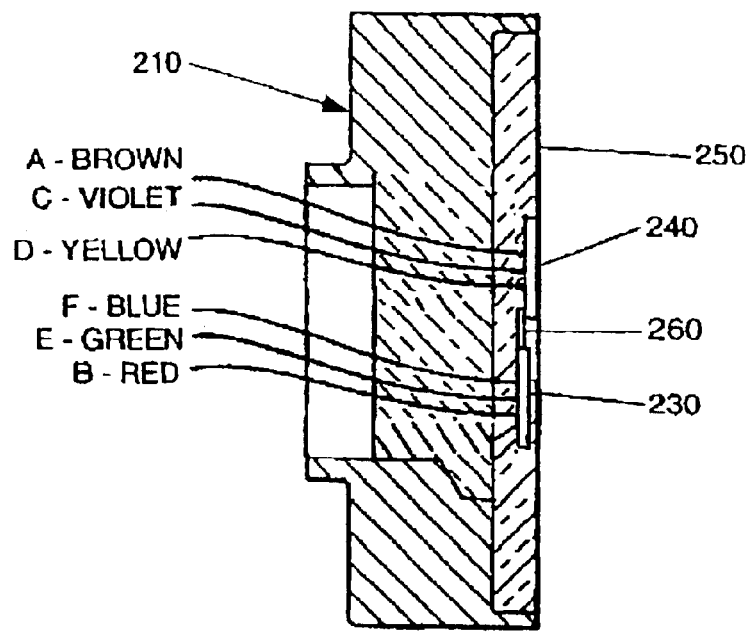
FIG. 10 depicts a side elevation of the unitized measurement probe of the preferred embodiment that is a total immersion probe.
Figure 11:
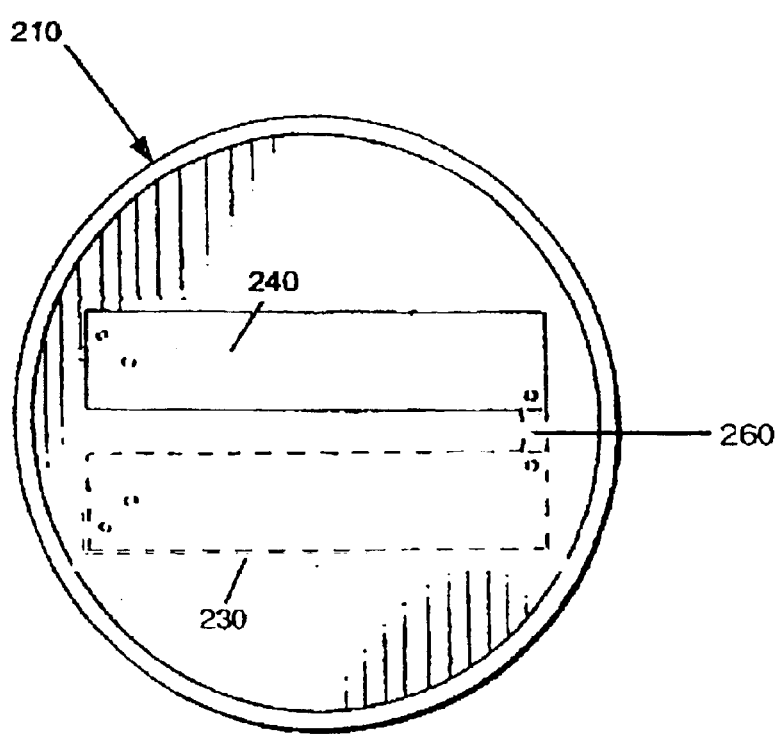
FIG. 11 shows an end view of the total immersion probe of FIG. 10.

As shown in FIGS. 10 and 11, the preferred embodiment of the present invention is comprised of a total immersion probe 210 consisting of a reference element 230 and the corroding element 240. A conformal protective coating 250, that protects the reference electrode from the corrosive activity of the fluid medium, completely covers the entire exposed surfaces of the reference elements 230.

When the probe is immersed in the corrosive fluid, there is a loss of metal in the corroding element. This loss of metal manifests itself as an increase in the resistivity of this electrode. This increase is then registered by the highly sensitive electronic measurement circuits to ultimately display the results on the liquid crystal display.

Figure 12:
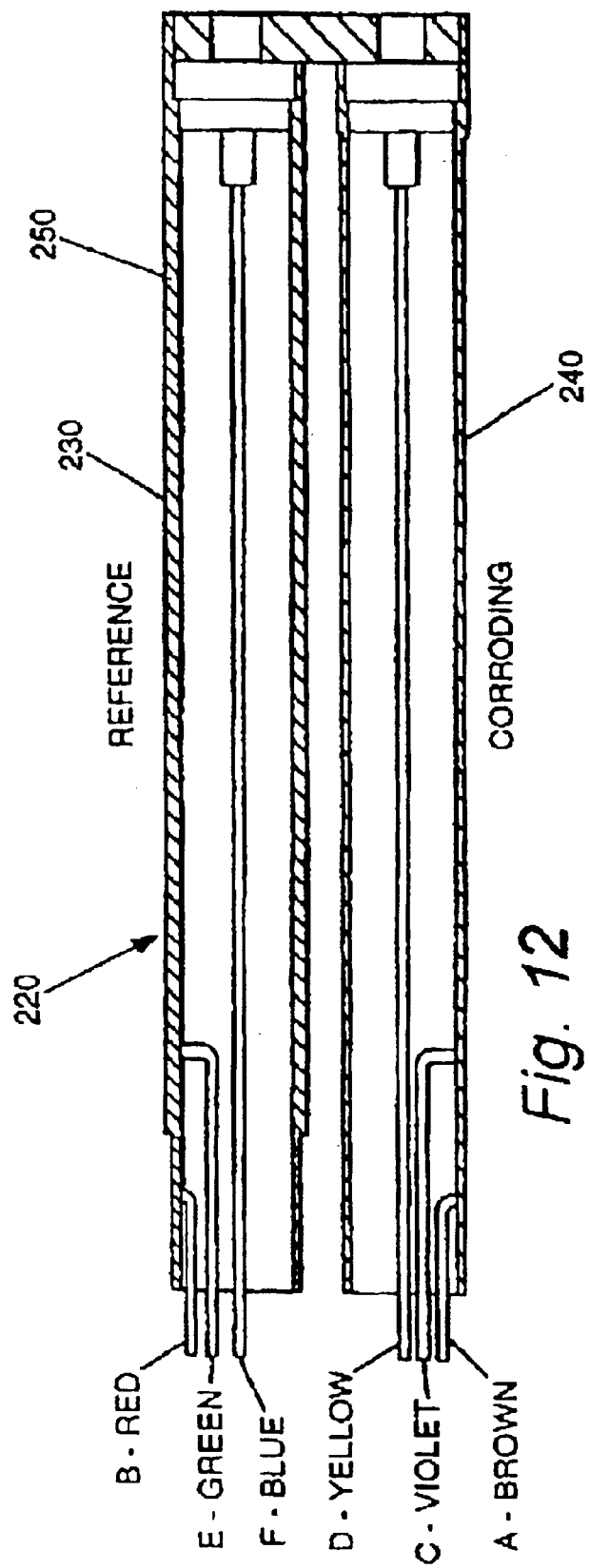
FIG. 12 depicts a side elevation of the unitized measurement probe of alternative embodiment that is a partial immersion probe, where only the ends of the probe are immersed in the fluid.
Figure 13:
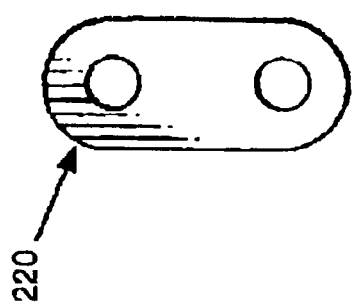
FIG. 13 shows an end view of the partial immersion probe of FIG. 12.

Shown in FIGS. 12 and 13 is the detailed assembly of an alternate embodiment of a partial immersion probe 220, where only the probe end comes in contact with the corrosive fluid medium. The probe body is shaped cylindrically as illustrated in FIG. 12, where only the probe tip is immersed into the corrosive fluid medium.

It should be understood that there may be numerous modifications, advances or changes that can be made to the present invention, but in doing so, it is intended that they should not detract from the true spirit of the present invention.

Parts List

100. Feedback control circuit
105. True differential input reference amplifier
110. High pass Filter
115. RMS-to-DC converter
120. Amplitude control
125. Sinusoidal oscillator
130. Voltage-to-current converter
135. True differential input corrosivity amplifier
140. High pass amplifier
145. RMS-to-DC converter
150. Forward path reference measurement channel
155. Analog-to-digital converter (ADC)
160. Forward path corrosion measurement channel
165. Cold junction reference temperature relay contacts
170. Reference element to reference channel relay contacts
175. Reference element to corrosivity channel relay contacts
180. Corrosivity element to corrosivity channel relay contacts
190. Feedback path channel
200. Temperature reference element
210. Total immersion probe
220. Partial immersion probe
230. Reference element
240. Corroding element
250. Conformal protective coating
260. Thermal bridge

I claim:

1. A corrosion measurement system for simultaneously determining the corrosivity and rate of corrosion of a particular fluid medium in real-time, comprising:
    a temperature compensated measurement circuit with a probe contacting the fluid medium, having a pair of substantially identical electrodes comprising a reference element and a corrosivity element, wherein each element is identical in mass, metallic composition and physical geometry;
    the circuit having input signals from each element, further comprising a means for maintaining a constant voltage across the reference element;
    a means for conditioning a primary reference element signal;
    a means for conditioning a corrosivity element measuring circuit signal;
    each of said means for conditioning having outputs to an ADC converter and to a microprocessor.

2. The corrosion measurement system according to claim 1, further comprising feedback control loop including a current regulator feedback circuit with a feedback regulator with an input signal derived from the probe reference element, thereby compensating for any temperature variation.

3. The corrosion measurement system according to claim 2, further comprising a forward path reference measurement channel and a forward path corrosion measurement channel.

4. The corrosion measurement system according to claim 3, the forward path reference measurement channel comprising a differential reference amplifier, a high pass filter, and an RMS-to-DC converter.

5. The corrosion measurement system according to claim 4, the forward path corrosivity measurement channel comprising a differential reference amplifier, a high pass filter, and an RMS-to-DC converter.

6. The corrosion measurement system according to claim 3, further comprising a temperature reference element communicating on a temperature reference channel of the circuit.

7. The corrosion measurement system according to claim 6, the temperature reference element having a voltage input to a differential amplifier, a high pass filter to remove all DC voltage components, and to RMS-to-DC converter having a low pass filter connected to its output, where an output channel connects to the negative input of the analog-to-digital converter and to the microprocessor.

8. The corrosion measurement system according to claim 6, further comprising a multiplexed switching arrangement including four independent switches for automatic activation of the respective channels of the system.

9. The corrosion measurement system according to claim 8, wherein a difference between the reference element signal and the corrosivity element signal is provided both at zero and at full scale, for self-calibration of the system.

10. The corrosion measurement system according to claim 9, the reference element comprising a fluid medium temperature determining element.

11. The corrosion measurement system according to claim 10, wherein the reference element and the corrosion element are connected in series.

12. The corrosion measurement system according to claim 11, the temperature reference connected in series with the reference element and the corroding element.

13. The corrosion measurement system according to claim 12, the current regulator feedback circuit comprising a forward path channel and a feedback channel.

14. The corrosion measurement system according to claim 13, the current regulator forward path channel comprising a differential reference amplifier, a high pass filter and an RMS converter.

15. The corrosion measurement system according to claim 14, the feedback path channel comprising an amplitude control sinusoidal oscillator and voltage to current converter.

16. The corrosion measurement system according to claim 13, further comprising a thermal bridge connecting the reference element and the corrosion element, whereby said elements are thermally connected to maintain a constant temperature between the reference and the corroding element to eliminate errors caused by thermal gradients.

17. The corrosion measurement system according to claim 13, wherein a temperature gradient between the reference element and the corroding element is essentially zero.

18. The corrosion measurement system according to claim 17, each element having a thermal inertia of its mass essentially equal to the other; and, a ratio of voltages across each element is thermally compensating, thereby eliminating errors due to a thermal tracking due to an equality of thermal inertia of the two masses.

19. The corrosion measurement system according to claim 18, wherein the reference element is coated with an impermeable material to prevent a corrosive medium from corroding it.

20. The corrosion measurement system according to claim 19, wherein the protective material coating of the reference element comprises thermal conduction and thermal transfer properties.

21. The corrosion measurement system according to claim 20, wherein the coating further comprises electrical insulating properties.

* * * * *